United States Patent [19]
Tsuda et al.

[11] Patent Number: 5,846,388
[45] Date of Patent: Dec. 8, 1998

[54] AZEOTROPIC MIXTURE OF 1,1-DIFLUOROETHANE AND HYDROGEN FLUORIDE AND PRODUCTION PROCESS OF 1,1-DIFLUOROETHANE

[75] Inventors: Takehide Tsuda; Satoshi Komatsu, both of Osaka, Japan

[73] Assignee: Daiken Industries Ltd., Osaka, Japan

[21] Appl. No.: 525,790

[22] PCT Filed: Apr. 5, 1994

[86] PCT No.: PCT/JP94/00558

§ 371 Date: Sep. 29, 1995

§ 102(e) Date: Sep. 29, 1995

[87] PCT Pub. No.: WO94/22796

PCT Pub. Date: Oct. 13, 1994

[30] Foreign Application Priority Data

Apr. 6, 1993 [JP] Japan ................................ 5-079488

[51] Int. Cl.[6] .............................. B01D 3/36; C07C 17/383
[52] U.S. Cl. ............................... 203/67; 203/91; 252/67; 252/DIG. 9; 423/488; 570/178
[58] Field of Search .................... 203/91, 39, 67, 203/50; 570/177, 178; 252/67, DIG. 9; 423/488

[56] References Cited

U.S. PATENT DOCUMENTS 4,818,513  4/1989  Trager et al. ........................ 423/488
4,944,846  7/1990  Manzer et al. ........................ 203/91
5,196,616  3/1993  Lee et al. ............................ 203/39
5,211,817  5/1993  Adams et al. ........................ 203/82
5,523,015  6/1996  Tsuda et al. ......................... 252/171
5,560,899  10/1996 Solinas et al. ...................... 570/177
5,626,725  5/1997  Balthasart et al. ................... 203/91

FOREIGN PATENT DOCUMENTS 0467531   1/1992  European Pat. Off. .
2310749   9/1974  Germany .
2-196734  8/1990  Japan .
5178768   7/1993  Japan .

*Primary Examiner*—Virginia Manoharan
*Attorney, Agent, or Firm*—Birch, Stewart, Kolasch & Birch, LLP

[57] ABSTRACT

There is provided an azeotropic mixture of hydrogen fluoride (HF) and 1,1-difluoroethane (HFC152a). In addition, there is provided a process for the production of HFC152a having a step of more effectively recovering HF which does not contain HFC152a or HFC152a which does not contain HF in which step an azeotropic mixture is distilled off from a column top by subjecting a mixture containing HFC152a and HF, so that HF which does not contain HFC152a or HFC152a which does not contain HF is recovered from a column bottom.

6 Claims, 1 Drawing Sheet

AZEOTROPIC MIXTURE OF 1,1-DIFLUOROETHANE AND HYDROGEN FLUORIDE AND PRODUCTION PROCESS OF 1,1-DIFLUOROETHANE

FIELD OF THE INVENTION

The present invention relates to an azeotropic mixture of 1,1-difluoroethane (which is, hereinafter, also referred to as "HFC152a") and hydrogen fluoride (which is, hereinafter, also referred to as "HF") and a production process of HFC152a comprising a step of recovering, from a mixture comprising HFC152a and HF, one component of HFC152a and HF which is substantially free from the other component of HFC152a and HF.

BACKGROUND OF THE INVENTION

HFC152a has been noteworthy as a substitute for 1-chloro-1,1-difluoromethane and it is useful as, for example, a foaming agent.

HFC152a is generally produced by reacting a chlorinated carbon such as vinyl chloride with HF in the presence of a catalyst in a vapor or liquid phase. During this reaction process, HF which has not been reacted remains in a reaction product.

As a manner to separate HF from the reaction product, a process has been hitherto used in which a mixture comprising a reaction product such as HFC152a and unreacted feed materials such as HF is washed with an aqueous phase to remove HF. However, such process requires a large amount of an alkali which is to be used for neutralization of the washing aqueous phase, and a waste from the neutralization has to be treated. Thus, such a process is not so useful.

It is, therefore, desirable to provide a production process of HFC152a comprising a step wherein HF which does not contain HFC152a or HFC152a which does not contain HF is more effectively recovered from a mixture comprising HF and HFC152a.

DETAILED DESCRIPTION OF THE INVENTION

Figure 1:
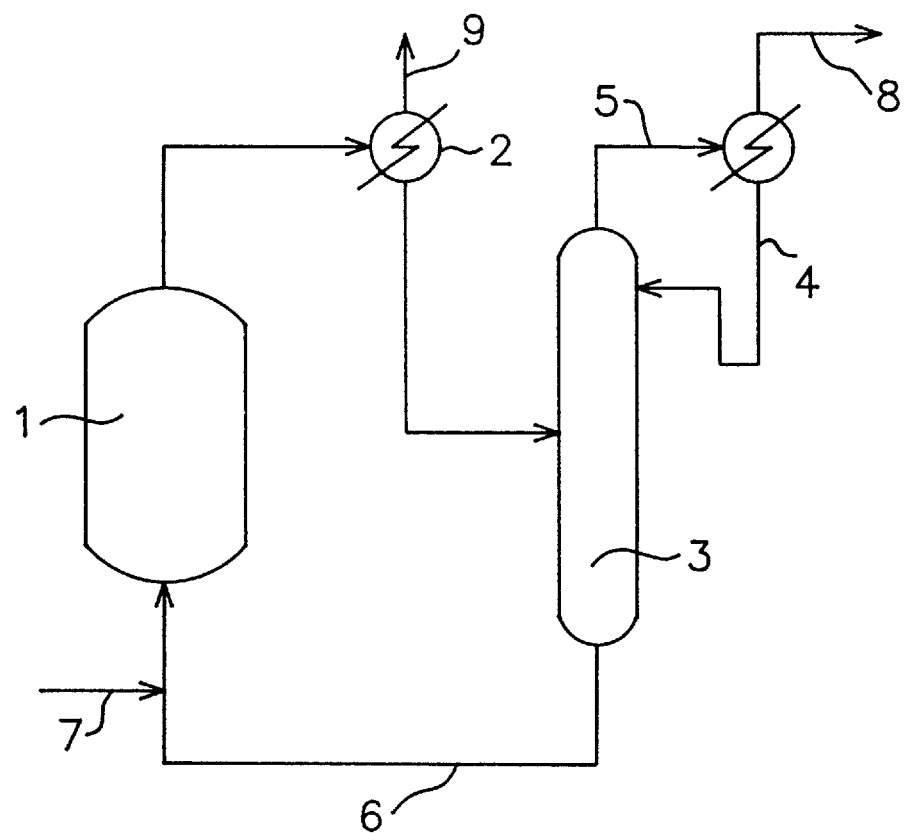
FIG. 1 shows a flow sheet of one embodiment of a process for the production of 1,1-difluorochloroethane in which the process according to the present invention is adopted.

The inventors have made extensive studies on a separation process of HF from a mixture comprising at least HF and HFC152a and found that HFC152a and HF forms a minimum azeotropic mixture and that the above problem is solved by utilizing the azeotropic mixture.

In the first aspect, the present invention, therefore, provides an azeotropic mixture consisting essentially of HFC152a and HF. This azeotropic mixture can be used as a reflux stream for a distillation operation which separates HF or HFC152a from a mixture comprising HFC152a and HF. That is, by subjecting the mixture comprising HFC152a and HF to the distillation operation, distilling off such an azeotropic mixture from a top of a distillation column as a distillate and returning a portion of the distillate to the distillation column, HF or HFC152a is effectively separated and removed from the mixture so that HFC152a which does not contain HF or HF which does not contain HFC152a can be recovered as a bottom product.

As described above, there is formed a (minimum) azeotropic mixture in a two component system of HFC152a and HF. Such an azeotropic mixture has been firstly found by the present inventors.

The above finding is based on observations that when a mixture of HFC152a and HF is subjected to a distillation operation under, for example, an atmospheric pressure, HFC152a cannot be further concentrated above an HFC152a/HF molar ratio of about 88/12. In other words, a composition of a liquid phase in such a state is the same as that of a vapor phase which is equilibrium with the liquid phase.

This azeotropic mixture has a boiling point of −45° C. at a pressure of 0.5 kg/cm$^2$-abs. and a composition of the mixture is about 15 mol % of HF and about 85 mol % of HFC152a. The azeotropic mixture has an azeotropic boiling point of −28° C. at an atmospheric pressure and an azeotropic composition of the mixture is about 12 mol % of HF and about 88 mol % of HFC152a. The azeotropic mixture has an azeotropic boiling point of about 45° C. at a pressure of 10 kg/cm$^2$-abs. and an azeotropic composition of the mixture is about 10 mol % of HF and about 90 mol % of HFC152a. The azeotropic mixture has an azeotropic boiling point of about 90° C. at a pressure of 30 kg/cm$^2$-abs. and an azeotropic composition of the mixture is about 8 mol % of HF and about 92 mol % of HFC152a. Under a pressure in a range of 0.5 kg/cm$^2$-abs. to 30 kg/cm$^2$-abs., the azeotropic composition depends on the pressure and it resides in an HF range of about 15 to 8 mol % and an HFC152a range of about 85 to 92 mol % and the azeotropic temperature is in the range of −45° to 90° C.

In the second aspect, the present invention provides a process for the production of HFC152a which comprises a step of removing a mixture of HFC152a and HF from a column top as an azeotropic mixture by directly subjecting a mixture comprising at least HF and HFC152a to a distillation operation so that HFC152a which does not substantially contain HF or a mixture comprising HFC152a which mixture does not substantially contain HF, or HF which does not substantially contain HFC152a or a mixture comprising HF which mixture does not substantially contain HFC152a is recovered from a column bottom.

In a particularly preferred embodiment according to the present invention, a mixture of HF and HFC152a is directly subjected to the distillation operation and HFC152a and HF is distilled off from the column top as the azeotropic mixture so that HFC152a which does not substantially contain HF or HF which does not substantially contain HFC152a is recovered from the column bottom.

In the drawing, the reference number 1 denotes a reaction vessel, 2 denotes a partial condenser, 3 denotes a distillation apparatus, 4 denotes a reflux stream, 5 denotes a distillate stream, 6 denotes a bottom product stream, 7 denotes a starting raw material stream, 8 denotes an azeotropic mixture product stream and 9 denotes a hydrogen chloride stream.

Since it has been found that HFC152a and HF form the azeotropic mixture, HFC152a which does not substantially contain HF can be effectively obtained from the column bottom by subjecting a starting mixture of HFC152a and HF to the distillation operation, distilling off the azeotropic mixture of HFC152a and HF from the column top and returning a portion the azeotropic mixture to the column top as a reflux stream in case in which a ratio of HF to HFC152a in the starting mixture is smaller than that in the azeotropic mixture of HFC152a and HF.

To the contrary, in case in which a ratio of HF to HFC152a in the starting mixture is larger than that in the azeotropic mixture of HFC152a and HF, HF which does not substantially contain HFC152a can be effectively obtained from the column bottom by, again, subjecting the starting mixture of HFC152a and HF to the distillation operation, distilling off the azeotropic mixture of HFC152a and HF from the column top and returning a portion the azeotropic mixture to the column top as the reflux stream.

Even in case in which the starting mixture further contains other component(s) in addition to HFC152a and HF, the process according to the present invention can be carried out. In such case, the distillation apparatus may be operated, depending on a relationship between a boiling point(s) of other component(s) and the azeotropic boiling point, in such a manner that other component(s) is concentrated in an enriching section or in a stripping section of the distillation apparatus. That is, in case in which the azeotropic boiling point is lower than the boiling point(s) of other component (s), the distillation apparatus can be operated in such a manner that other component(s) is concentrated in the stripping section, and thus contained and recovered in the bottom product. To the contrary, in case in which the azeotropic boiling point is higher than the boiling point(s) of other component(s), the distillation apparatus can be operated in such a manner that other component(s) is concentrated in the enriching section, and thus contained and recovered in the distillate product.

The distillation apparatus used for the above separation operation may be of any type provided that it has functions which are necessary for a general distillation operation. For example, a fractionation apparatus comprising for example a plate column, a packed column and the like may be used to obtain particularly preferred results. Either of a batch distillation operation or a continuous distillation operation may be possible.

Distillation conditions are not particularly limited. Generally, from a view point of energy consumption, an optimum column top temperature and an optimum column bottom temperature and an optimum operation pressure of the distillation apparatus are determined. Usually, the operation pressure is selected from a range of 0.5 kg/cm$^2$-abs. to 30 kg/cm$^2$-abs. In such pressure range, the column top temperature is in a range of about −45° C. to 90° C. The column bottom temperature is a boiling point of HF or HFC152a under the operation pressure provided that no pressure loss is taken into account.

The process according to the present invention is the most useful when it is adopted in the case in which HF is recovered from a reaction mixture comprising HFC152a and a large amount of unreacted HF which mixture has been produced through a fluorination reaction of vinyl chloride with a highly excessive amount of HF in the presence of a catalyst in a vapor phase and the recovered HF is reused for the reaction.

A preferred embodiment will be, hereinafter, explained in which the process according to the present invention is utilized for the reaction as described just above.

FIG. 1 is also applicable to the preferred embodiment of a production process of HFC152a according to the present invention which process comprises the recovery step of HF.

In a reaction vessel 1, vinyl chloride and HF supplied as a stream 7 react, and a reaction product mixture is withdrawn usually as a vapor phase from the reaction vessel 1. The produced reaction mixture comprises HFC152a, 1-chloro-1-fluoroethane (which is, hereinafter, also referred to as "HCFC151a"), vinyl chloride, HF and hydrogen chloride. After hydrogen chloride is removed from the mixture in a partial condenser 2 as a stream 9, the mixture comprising HFC152a, HCFC151a, vinyl chloride and HF is introduced into a distillation apparatus 3.

In the mixture of which hydrogen chloride content has been removed, HF is present in large excess of HF in the azeotropic composition (for example, 0 to 90 mol % of HF and about 10 to 20 mol % of HFC152a). Therefore, HF and HFC152a of the azeotropic composition are distilled off from the top of the distillation apparatus 3 (stream 5) and a portion thereof is returned to the top of the distillation apparatus 3 as a reflux (stream 4).

By the distillation operation as above, a mixture comprising HF, HCFC151a and vinyl chloride which mixture does not substantially contain HFC152a is withdrawn as a bottom product (stream 6) from the distillation apparatus 3.

The obtained bottom product (stream 6) is further subjected to an additional treatment(s) (for example, additional distillation, extraction and the like) so as to remove impurities therein or directly mixed with the reaction starting raw materials (vinyl chloride and hydrogen fluoride, stream 7) which are freshly supplied, and then reused in the reaction vessel 1.

A rest of the azeotropic mixture which has been deducted by an amount of the reflux is obtained as a stream 8 of HF and HFC152a having the azeotropic composition, which stream is further treated so as to finally obtain HFC152a (by, for example, additional distillation, HF absorption and the like).

In this way, HF can be effectively recovered from the mixture comprising HFC152a and HF.

The above operation may be carried out batch-wise, but it is more effective to carry out continuously as shown in FIG. 1.

EXAMPLES

The present invention will be, hereinafter, explained in detail with reference to Examples.

Example 1

132 Grams (2 mol) of HFC152a and 1 g (0.05 mol) of HF were charged into a distillation column made of stainless steel (a packed column having a still volume of 600 ml, a diameter of 20 mm and a height of 1 m), and the distillation operation was initiated at a total reflux condition under a superatmospheric pressure. When a top pressure of the column reached 10 kg/cm$^2$-abs. and also a top temperature reached 45° C., a sample of the liquid distillate was obtained. The sample was analyzed with the result that a molar ratio of HFC152a/HF was 90/10.

From the above analysis results, it has been clarified that HF having a boiling point which is higher than that of HFC152a (HFC152a's boiling point at an atmospheric pressure 24.7° C.<HF's boiling point at an atmospheric pressure 19.5° C.) is concentrated in the top section of the column and that HFC152a and HF thus forms the minimum azeotropic mixture.

Further, similar experiments were carried out with changing the operation pressure and different azeotropic compositions were obtained, of which results are shown in Table 1 below:

TABLE 1

| Top Pressure (kg/cm$^2$-abs.) | Top Temperature (°C.) | HFC152a/HF Azeotropic Composition (mol %) |
|---|---|---|
| 3 | 0 | 89/11 |
| 8.5 | 40 | 89.5/10.5 |
| 10 | 45 | 90/10 |
| 30 | 90 | 92/8 |

Example 2

198 Grams (3 mol) of HFC152a and 1 g (0.05 mol) of HF were charged into the same distillation apparatus as in Example 1 and the apparatus was operated and stabilized with a total reflux condition at a top temperature of 45° C. under a top pressure of 10 kg/cm$^2$-abs. After the operation was stabilized, the liquid distillate was withdrawn little by little from the top of the column and then the top temperature increased gradually. When the top temperature reached a temperature which was the same as the still (bottom) temperature, heating was stopped. An amount of the liquid withdrawn from the column top was about 50 g, and about 130 g of HFC152a was withdrawn from the still which contained about 30 ppm of HF.

Example 3

165 Grams (2.5 mol) of HFC152a and 200 g (10 mol) of HF were charged in the same distillation apparatus as in Example 1 and the apparatus was operated and stabilized with a total reflux condition at a top temperature of 45° C. under a top pressure of 10 kg/cm$^2$-abs. After the operation was stabilized, the liquid distillate was withdrawn little by little from the top of the column and then the top temperature increased gradually. When the top temperature reached a temperature which was the same as the still temperature, heating was stopped. An amount of the liquid withdrawn from the column top was about 205 g, and about 150 g of HFC152a was withdrawn from the still which contained about 50 ppm of HF.

We claim:

1. An azeotropic mixture consisting essentially of 1,1-difluoroethane and hydrogen fluoride.

2. The azeotropic mixture according to claim 1 wherein under a pressure in a range of 0.5 kg/cm$^2$-abs. to 30 kg/cm$^2$-abs., the mixture has a hydrogen fluoride/1,1-difluoroethane molar ratio in a range of 15/85 to 9/92 mol % and a boiling point in a range of −45° to 90° C.

3. A process for recovering hydrogen fluoride which comprises distilling off an azeotropic mixture of 1,1-difluoroethane and hydrogen fluoride by subjecting a mixture comprising at least 1,1-difluoroethane and hydrogen fluoride to a distillation operation, and withdrawing a bottom product comprising hydrogen fluoride which product does not contain 1,1-difluoroethane.

4. The process according to claim 3 wherein the distillation operation is conducted at a pressure in a range of 0.5 kg/cm$^2$-abs. to 30 kg/cm$^2$-abs.

5. A process for recovering 1,1-difluoroethane from an azeotropic mixture of 1,1-difluoroethane and hydrogen fluoride which comprises distilling off said azeotropic mixture of 1,1-difluoroethane and hydrogen fluoride by subjecting a mixture comprising at least 1,1-difluoroethane and hydrogen fluoride to a distillation operation, and withdrawing a bottom product comprising 1,1-difluoroethane which product does not contain hydrogen fluoride.

6. The process according to claim 5 wherein the distillation operation is conducted at a pressure in a range of 0.5 kg/cm$^2$-abs. to 30 kg/cm$^2$-abs.

* * * * *

UNITED STATES PATENT AND TRADEMARK OFFICE
CERTIFICATE OF CORRECTION

PATENT NO. : 5,846,388
DATED : December 8, 1998
INVENTOR(S) : Takehide TSUDA et al.

It is certified that error appears in the above-indentified patent and that said Letters Patent is hereby corrected as shown below:

On the title page, Item [73],

Please change

"[73] Assignee: Daiken Industries Ltd., Osaka, Japan"

to

--[73] Assignee: Daikin Industries Ltd., Osaka, Japan--

Signed and Sealed this

Twenty-second Day of June, 1999

Attest:

Q. TODD DICKINSON

*Attesting Officer*     Acting Commissioner of Patents and Trademarks